United States Patent [19]

Baldwin et al.

[11] Patent Number: 5,196,318
[45] Date of Patent: Mar. 23, 1993

[54] PRECISELY REGULATED EXPRESSION OF DELETERIOUS GENES

[75] Inventors: Thomas O. Baldwin, Bryan; Jerry H. Devine; Gerald S. Shadel, both of College Station, all of Tex.

[73] Assignee: The Texas A&M University System, College Station, Tex.

[21] Appl. No.: 544,268

[22] Filed: Jun. 26, 1990

[51] Int. Cl.$^5$ .................. C12P 21/00; C12N 15/09; C12N 15/70; C12N 15/31
[52] U.S. Cl. ................... 435/69.1; 435/172.3; 435/320.1; 536/27
[58] Field of Search ............... 435/320.1, 172.3, 69.1; 536/27

[56] References Cited

U.S. PATENT DOCUMENTS

| | | | |
|---|---|---|---|
| 4,503,142 | 3/1985 | Berman et al. | 435/6 |
| 4,578,355 | 3/1986 | Rosenberg | 435/320.1 |
| 4,634,678 | 1/1987 | Salstrom et al. | 435/320.1 |
| 4,677,064 | 6/1987 | Mark et al. | 435/69.1 |
| 4,767,708 | 8/1988 | Minkley, Jr. et al. | 435/194 |
| 4,775,630 | 10/1988 | Tibbetts et al. | 435/320.1 |
| 4,782,022 | 11/1988 | Puhler et al. | 435/172.3 |

OTHER PUBLICATIONS

Raab, et al. (Sep. 1986), "Mutational analysis of bacteriophage lambda lysis gene S", J. Bacteriol. 167, 1035-1042.

Engebrecht et al. (1987), "Nucleotide sequence of the regulatory locus controlling expression of bacterial genes for bioluminescence", Nuc. Acids Res. 15, 10455-10467.

Adhya, et al., "The Role of Gene S", (1971) *Bacteriophage Lambda*, pp. 743-746, Cold Spring Harbor Laboratory, Cold Spring Harbor, N.Y.

Baldwin et al., "The Complete Nucleotide Sequence of the lux Regulon of *Vibrio fischeri* and the luxABN Region of Photobacterium leiognathi and Mechanism of Control of Bacterial Bioluminescence" (1989) *J. Biolum. Chemilumin.*, 4:326-341.

Bedwell and Nomura, "Feedback regulation of RNA polymerase subunit synthesis after the conditional overproduction of RNA polymerase in Escherichia coli", (1986) *Mol. Gen. Genet.* 204:17-23.

Coleman et al., "Baceriophage MS2 Lysis Protein Does Not Require Coat Protein to Mediate Cell Lysis," (1983) *J. Bacteriol.*, 153:1098-1100.

Devine et al., "Nucleotide Sequence of the luxR and luixI Genes and Structure of the Primary Regulatory Region of the lux Regulon of *Vibrio Fischeri*, ATCC 7744," (1988) *Biochemistry*, 27:837-842.

Devine et al., "Identification of the operator of the lux regulon from the *Vibrio fischeri* strain ATCC7744," (1989) *Proc. Natl. Acad. Sci. USA*, 86:5688-5692.

Dunlap and Greenberg, "Control of *Vibrio fischeri* Luminescence Gene Expression in *Escherichia coli* by Cyclic AMP and Cyclic AMP Receptor Protein," (1985) *J. Bacteriol.* 164:45-50.

Dunlap and Greenberg, "Control of *Vibrio fischeri* lux Gene Transcription by Cyclic AMP Receptor Protein--LuxR Protein Regulatory Circuit" (1988) *J. Bacteriol.*, 170:4040-4046.

(List continued on next page.)

*Primary Examiner*—Richard A. Schwartz
*Assistant Examiner*—Philip W. Carter
*Attorney, Agent, or Firm*—Arnold, White & Durkee

[57] ABSTRACT

The invention relates to an expression vector system based on the regulation of bacterial luminescence (the lux gene system). The invention further relates to the construction of a precisely regulatable expression vector system which comprises a complete luxR gene in combination with an inactivated luxI gene. If the system is turned off, no significant transcription occurs of any cloned gene product when used in combination with the regulatory scheme of the invention as is demonstrated by using the bacteriophage λ lysis genes. The induction of transcription relies on the addition of exogenous autoinducer which is both inexpensive and easy-to-use and which is required in only minute amounts.

15 Claims, 2 Drawing Sheets

OTHER PUBLICATIONS

Eberhard, "Inhibition and Activation of Bacterial Luciferase Synthesis," (1972) *J. Baceriol.* 109:1101–1105.

Eberhard, "Structural Identification of Autoinducer of Photobacterium *fischeri* Luciferase," (1981) *Biochemistry*, 20:2444–2449.

Eberhard et al., "Analogs of the autoinducer of bioluminescence in *Vibrio fischeri*," (1986) *Arch. Microbiol.*, 146:35–40.

Engebrecht, et al., "Bacterial Bioluminescence: Isolation and Genetic Analysis of Functions from *Vibrio fischeri*", (1983) *Cell* 32:773–781.

Engebrecht and Silverman, "Identification of genes and gene products necessary for bacterial bioluminescence," (1984) *Proc. Natl. Acad. Sci. USA* 81:4154–4158.

Engebrecht and Silverman, "Regulation of Expression of Bacterial Genes for Bioluminescence," In J. K. Setlow and A. Hollaender (eds.), (1986) *Genetic Engineering*, 8:31–44.

Goldberg and Howe, "New Mutations in the S Cistron of bacteriophage Lambda Affecting Host Cell Lysis," (1969) *Virology* 38:200–202.

Hastings and Weber, "Total Quantum Flux of Isotropic Sources," (1963) *J. Opt. Soc. Am.*, 53:1410–1415.

Henikoff, et al., "Finding Protein Similarities with Nucleotides Sequence Databases" (1990) *Methods Enzymol.* 183:111–132.

Humphreys, et al., "Mutagenesis of Plasmid DNA with Hydroxylamine: Isolation of Mutants of Multi-copy Plasmids," (1976) *Mol. Gen. Genet.* 145:101–108.

Joachimiak, et al. "Purification and Characterization of trp aporepressor," (1983) *Proc. Natl. Acad. Sci. USA* 80:668–672.

Kaplan, et al. "Synthesis of N-[3-OXO-(4,5-$^3$H$_2$)-HEXANOYL] homoserine lacone: Biologically Active Tritium-Labelled *Vibrio Fischeri* Autoinducer," (1985) *J. Labelled Compd. Radiopharm.* 22:387–395.

Kaplan and Greenberg, "Diffusion of Autoinducer Is Involved in Regulation of the *Vibrio fischeri* Luminescence System," (1985) *J. Bacteriol.*, 163:1210–1214.

Kaplan and Greenberg, "Overproduction and purification of the luxR gene product: Transcriptional activator of the *Vibrio fischeri* luminescence system," (1987) *Proc. Natl. Acad. Sci. USA* 84:6639–6643.

Konisky, "Colicins and Other Bacteriocins with Established Modes of Action," (1982) *Ann. Rev. Microbiol.*, 36:125–144.

Lanzer and Bujard, "Promoters largely determine the efficiency of repressor action," (1988) *Proc. Natl. Acad. Sci. USA* 85:8973–8977.

Meighen, "Enzymes and Genes From The lux Operons of Bioluminescent Bacteria," (1988) *Ann. Rev. Microbiol.* 42:151–176.

Michaelis and Beckwith, "Mechanism of Incorporation of Cell Envelope Proteins in *Escherichia coli*," (1982) *Ann Rev. Microbiol.* 36:435.

Rosenberg et al. "Gene Amplification & Analysis," (1981) In, *J. G. Chirikjian* (ed.) pp. 132–164.

Shadel et al., "Use of Regulated Cell Lysis in a Lethal Genetic Selection in *Escherichia coli*: Identification of the Autoinducer-Binding Region of the LuxR Protein from *Vibrio fischeri* " ATCC 7744, (1990) *J. Bacteriol.* 172:3980–3987.

Slock et al., "Critical Regions of the *Vibrio fischeri* LuxR Protein Defined by Mutational Analysis," (1990) *J. Bacteriol.* 172:3974–3979.

Tabor and Richardson, "DNA sequence analysis with a modified bacteriophage T7 DNA polymerase," (1989) *Proc. Natl. Acad. Sci. USA* 84:4767–4771.

Ulitzur, "The Regulatory Control of the Bacterial Luminescence System—A New View," (1989) *J. Biolumin. Chemilumin.* 4:317–325.

Ulitzer and Kuhn, "The Transcription of Bacterial Luminescence is Regulated by Sigma 32," (1988) *J. Biolumin. Chemilumin.* 2:81–93.

Kemper and Hanson, "Aspects of Light Production by Photobacterium *fischeri*," (1968) *J. Bacteriol.* 95:975–979.

Nealson et al., "Catabolite Repression of Bacterial Bioluminescence: Functional Implications," (1972) *Proc. Nat. Acad. Sci. USA* 69:1073–1076.

Nealson et al., "Cellular Control of the Synthesis and Activity of the Bacterial Luminescent System," (1970) *J. Bacteriol.* 104:313–322.

PRECISELY REGULATED EXPRESSION OF DELETERIOUS GENES

BACKGROUND OF THE INVENTION

The National Science Foundation provided funding used in part for this for this invention under grant RF 5311. Accordingly, the Federal Government may have certain rights in this invention pursuant to 35 U.S.C § 202.

1. Field of the Invention

The invention relates to an expression vector system based on the regulation of bacterial luminescence (the positive feedback lux regulatory circuit). The invention further relates to the construction of a precisely regulatable expression vector system which comprises a complete luxR gene in combination with an inactivated luxI gene, both of which are under the control of a common control region. The invention allows the precise temporal expression of gene products otherwise deleterious or lethal to the cell when controlled by standard expression systems. The invention further relates to the control of the expression system of the invention by an inexpensive inducer.

2. Description of the Related Art

Numerous expression systems exist for expression of gene products in bacteria. However, cloning and expression of genes which have deleterious effects on or which kill the cells in which they are expressed represents a continuing problem. Among these problem genes are a wide array of genes whose effects on the cell range from mildly deleterious to those gene products which are lethal to the cell in even minute quantities. As used herein, a deleterious gene is any gene whose expression in host cells in culture would prevent that culture from achieving the normal logarithmic growth which the culture would achieve but for the expression of the deleterious gene. Furthermore, as used herein, an expression system which is capable of stringently controlling the expression of such deleterious genes is an expression system which can sufficiently limit the expression of the deleterious gene in host cells in culture in order to allow the culture to achieve normal logarithmic growth which the culture would not achieve without the stringent control due to some level of transcription of the deleterious gene. Thus, in the case of genes whose products are lethal to the cell in even minute quantity, stringent control is that level of control which almost completely eliminates transcription of the lethal gene until released from that control.

Some deleterious genes encode gene products which if expressed in limited quantity are actually useful to the cell while if expressed in even slightly elevated quantities are deleterious to the cell. For example, such genes are epitomized by DNA-modifying enzymes such as the DNA restriction enzymes used throughout molecular biology. If allowed to be expressed in a host which is not resistant to the restriction enzyme, the host cell's own DNA is susceptible to degradation by the cloned gene's product (Rosenberg et al. 1981).

Even where a particular gene product merely stresses the host cell by its presence or by its overabundance, the production of these proteins in the cell may not be feasible. Such an effect has been observed, for instance, with overproduction of several of the subunits of E. coli RNA polymerase. Although it has been possible to overproduce the RNA polymerase subunits in host cells, their overexpression causes a reduction in growth rate of cultures of these cells (Bedwell and Nomura, 1986). These mildly deleterious effects represent enough of a stress to the population of cells that cells within that population, which contain a mutated version of the desired protein whose production has fewer or no deleterious effects compared to the non-mutated protein, may overgrow those cells containing the wild type protein.

Even more deleterious gene products include many proteins which become associated with the membrane of the host cells, some of which effect the cell to such a degree that the host cells are killed (Michaelis and Beckwith 1982). Some genes, in fact, code for proteins which, if expressed to any degree, even at levels as low as a few molecules of the protein per cell, lead quickly to the death of the host cell. These type of genes are typified by the class of genes encoding the lysis proteins of viruses (e.g., λ lysis protein or MS2 lysis protein) and the lytic proteins of bacteria (e.g., colicins of certain enteric bacteria) (Coleman et al. 1983; Adhya et al. 1971; Konisky 1982).

A number of patented expression systems for use in bacterial hosts have been described. In some cases, the expression systems relate to generalized expression systems. In others, specific positive regulation systems have been described. Other patented expression systems have been designed to allow relatively tight regulation. In some instances, these expression systems were individually tailored for expression of a particular protein which presented some difficulty using standard expression systems.

For instance, U.S. Pat. No. 4,782,022 appears to relate to the construction of a vector comprising a promoter of a constitutively expressed gene coupled to a gene which codes for a product capable of activating other genes required for nitrogen fixation. U.S. Pat. No. 4,775,630 appears to relate to a variant of an adenovirus control region, the regulator of which is especially sensitive to repression by products of the gene under its control. U.S. Pat. No. 4,767,708 appears to relate to the construction of a recombinant vector containing a cloned bacterial DNA polymerase I under operable control of a conditionally controllable foreign promoter. This patent notes that the foreign promoter may be a positively regulated promoter. The invention appears to be designed to overproduce DNA polymerase. U.S. Pat. No. 4,677,064 appears to relate to the use of the promoters of bacteriophage λ, $P_L$ and $N_{RBS}$, in order to construct a vector capable of overexpressing human tumor necrosis factor. U.S. Pat. No. 4,634,678 appears to relate to construction of a variety of expression vectors all of which are based upon negative control systems. The patent's specification does, however, suggest the replacement of negative control sequences with positive control sequences. U.S. Pat. No. 4,578,355 appears to relate to the use of the $P_L$ promoter of bacteriophage λ to construct a high level expression vector. U.S. Pat. No. 4,503,142 appears to relate to the construction of a class of cloning and expression vectors capable of heterologous gene expression. These vectors are based on the use of the lac promoter/operator of Escherichia coli (E. coli).

All of these systems suffer, to greater or lesser degrees, from the inability to control expression to the extent required when the gene product will kill or otherwise seriously damage the host cell if expressed. The analogy can be drawn to an electrical switch connected functionally to a device capable of inflicting great harm to those which encounter it, even if the amount of electricity reaching the device is minimal. The design electrical engineer would find it most unsatisfactory if the only switches available were those which constantly fed the lethal device small amounts of power. Moreover, even where the prior art expression systems have provided a means for limited expression of certain deleterious genes, the likelihood that the gene will mutate in order to prevent the deleterious effects on the host cell from being realized has always caused concern. This is especially true where large scale operations have been envisioned.

Additionally, many of the prior art expression systems must rely for induction of expression either on the host's biochemical responses or on costly or awkward induction means. Moreover, many prior art expression systems suffer from the fact that the inducer is a compound routinely found in nature such as naturally occurring sugar compounds. Thus, great care must be taken to prevent inadvertent exposure of cells to extraneous sources of such commonly encountered inducers.

The present inventors are involved in research into regulation of bioluminescence in the marine bacterium *Vibrio fischeri*, which regulation has been studied extensively through cloning and genetic manipulation of the lux system in *E. coli* (Devine et al. 1989; Dunlap and Greenberg 1985; Dunlap and Greenberg 1988; Engebrecht et al. 1983; Engebrecht and Silverman 1984; Engebrecht and Silverman 1986). Expression of the lux genes in *V. fischeri* is controlled by a unique form of positive feedback regulation called autoinduction, and this pattern of regulation may be duplicated by the cloned system in *E. coli* (Engebrecht et al. 1983; Engebrecht and Silverman 1986). The autoinduction response is mediated by the production and accumulation of a small molecule, the autoinducer, which is synthesized in the presence of the luxI gene product. This product molecule presumably interacts with the luxR gene product to induce the synthesis of the enzymes required for light production. Kaplan and Greenberg (1987) were able to overproduce the luxR gene product in *E. coli*, develop a procedure for purifying this overproduced protein, but were unable to demonstrate convincingly that LuxR protein had DNA-binding activity.

The autoinducer of *V. fischeri* has been identified as N-(3-oxo-hexanoyl) homoserine lactone (Eberhard et al. 1981) and has been shown to be both freely diffusible across the cytoplasmic membrane and species specific in its ability to stimulate bioluminescence (Eberhard 1972; Kaplan and Greenberg 1985). This molecule has been synthesized in vitro and shown to function in a biological assay (Eberhard et al. 1981; Kaplan et al. 1985).

The lux genes are organized into two divergently transcribed operons, termed rightward and leftward, which are separated by a common regulatory region (Devine et al. 1988; Engrebrecht et al. 1983; Engebrecht and Silverman 1987). The luxR gene is the only known gene in the leftward operon (operon$_L$) and encodes a positive regulatory protein which, in the presence of autoinducer, stimulates transcription of the rightward operon (operon$_R$). This interaction has recently been shown to require the 20-base-pair lux operator located in the control region (Devine et al. 1989). Operon$_R$ consists of at least six genes (luxICDABE). The luxI gene encodes a protein required for autoinducer synthesis (Engebrecht and Silverman 1984), the luxC, luxD, and luxE genes encode enzymes which provide luciferase with an aldehyde substrate (Meighen 1988), and the luxA and luxB genes encode the α and β subunits of the luciferase enzyme. The sequence of the entire lux regulon from *V. fisheri* has been determined (Baldwin et al. 1989).

The current model describing the autoinduction process suggests that a low basal level of transcription of operon$_R$ leads to low-level synthesis of autoinducer by luxI. High cell density is required for autoinducer to accumulate, since it is freely diffusible across the cytoplasmic membrane. It is by virtue of the diffusible nature of autoinducer that the expression of luminescence is, in nature, cell density-dependent. If the LuxR protein, whose synthesis is regulated at the transcriptional level by the cyclic AMP-catabolite gene activator protein (cAMP-CAP) system (Dunlap and Greenberg 1985; Dunlap and Greenberg 1988), has also accumulated, it can form a complex with autoinducer capable of binding to the lux operator and stimulating transcription of operon$_R$. Positive feedback results from the presence of luxI in operon$_R$, since stimulation of rightward transcription of luxR and autoinducer leads to the production of more autoinducer by increased levels of LuxI protein. In addition to this primary regulatory circuit, several global regulatory systems in *E. coli* have been shown to interact with the lux system to affect the timing of induction of bioluminescence including the heat shock ($\sigma^{32}$) system and the SOS response (Ulitzur 1989; Ulitzer and Kuhn 1988). Thus, the positive feedback mechanism of the lux regulatory circuitry leads to the sharp induction of the enzymes required for light production.

Expression systems are needed which do not rely for their induction on expensive or otherwise inadequate induction mechanisms. This is especially important for commercial operation of bacterial fermentations of useful gene products. More importantly, however, expression systems are needed which are capable of very stringently regulating the expression of deleterious or lethal genes until such time as induction of expression can be used to express commercial quantities of their otherwise harmful gene products. If such systems were available, the expression and genetic manipulation of a wide array of otherwise lethal or deleterious gene products would be possible via the powerful capabilities of batch fermentation.

SUMMARY OF THE INVENTION

The present invention relates to an expression system capable of stringently regulating the expression of deleterious or lethal genes until such time as induction of expression can be used to express high levels of the harmful gene products. The present invention further relates to expression systems which need not rely for their induction on inadequate induction mechanisms which are typically bulky, expensive or both. The present invention, therefore, further relates to systems for the expression of a wide array of otherwise lethal or deleterious gene products using bacterial fermentation.

More specifically, the present invention relates to the construction of vectors which retain an intact luxR gene and regulatory region but which lack intact copies of all of the genes in operon$_R$, retaining only a truncated luxI gene. This arrangement affords a very stringently regulated system in which operon$_R$ transcription is controlled by the addition of an inexpensive, synthetic inducer (autoinducer), but which system now lacks the positive-feedback mechanism. A potentially lethal transcriptional fusion of the lysis genes (S,R,R$_z$) from bacteriophage λ was created in operon$_R$ by insertion downstream of the truncated luxI gene in order to test the ability of this system to express a very lethal gene.

Such an expression system possesses two key attributes which distinguish the invention over the prior art. First, the transcription system of the invention is not as leaky as are those of the prior art. If the system is turned off, no significant transcription occurs of any cloned gene product when used in combination with the regulatory scheme of the invention. The surprising and unexpected level to which regulation can be controlled with this system was demonstrated convincingly by using the bacteriophage λ lysis genes. These bacteriophage lysis gene products are lethal to bacteria where even low transcription levels are allowed. Only a system which almost thoroughly stops transcription can be used to express such lethal proteins.

Coupled with the novel expression system, the second distinguishing attribute of the invention relates to the nature of the event which turns on transcription. The present inventors and others have found that other expression systems use either awkward or expensive events to stimulate synthesis of the cloned gene product. The stimulatory event of the present invention, however, relies on the addition of exogenous autoinducer which is both inexpensive and easy-to-use and which is required in only minute amounts. Additionally, this compound is not found routinely in nature avoiding problems of inadvertent induction found in prior art systems.

The present inventors set out to develop a flexible prokaryotic expression system utilizing the regulatory genes isolated from the marine bacterium *Vibrio fischeri*. The present inventors knew that *V. fischeri* displayed both a dramatic increase in the rate of luciferase synthesis following induction, apparently due to a unique positive feedback mechanism, and an enormous difference (ca. $10^5$) in levels of luminescence in cells before and after induction. The present inventors have demonstrated that a 20 base pair inverted repeat, ACCTGTAGGA$^x$TCGTACAGGT, is the binding site for the LuxR-autoinducer complex. They have also found that deletion of sequences upstream of the palindrome leads to increased transcription from the rightward promoter, indicative of a cis-acting element(s) that represses transcription in the absence of LuxR:autoinducer. Modifications of the palindrome that eliminate stimulation by LuxR:autoinducer of transcription from $P_R$ have no effect on repression by the cis-acting mechanism(s), suggesting that the palindrome is not necessary for repression of the rightward operon. Thus, it appears that the large increase in transcription upon induction of the lux regulon is the result of at least two independent mechanisms, one positive and the other negative. These unexpected findings lead to the realization that a unique system of expression might be possible which would allow a very stringent control of genes functionally connected to such an expression system.

The objective of the present inventors has been, therefore, to design and construct a unique vector in which induction is controlled by the addition of autoinducer. The requirement for autoinducer is accomplished by deletion of the luxI gene so that expression of the cloned gene can only be accomplished by addition of autoinducer. The basal level of rightward transcription is very low because the lux system is tightly repressed in the absence of autoinducer. This is an important consideration if the protein of interest is toxic to the host. Expression can be postponed until late in growth without adversely affecting the bacterium. This point was made very clear by the unexpectedly successful cloning and expression of the lysis genes from bacteriophage λ under control of operon$_R$ which allows control of cell lysis by autoinducer addition. In the absence of autoinducer, these lethal genes can be propagated without adversely affecting the host cells.

Accordingly, an expression system has been invented which consists of a lux regulatory circuit connected to and capable of stringently regulating expression of a gene. In a preferred embodiment of the present invention, at least one product of the cloned gene will be deleterious to the host cells used to express the gene. The deleterious effect may be one which directly occurs as a result of the presence of the gene product in the cell such as with a lysis protein. However, the deleterious effect may equally well be an indirect effect such as where membrane jamming occurs which eventually leads to the death of a cell.

The expression system may be used independent of other regulatory systems. Alternatively, one embodiment of the invention would include the use of the lux expression system operably linked to a second regulatory system or systems in order to achieve control of the second regulatory system by the lux expression system.

In this manner, the binding of the LuxR-autoinducer complex can also be adapted to perform a negative regulatory role. If the recognition sequence for LuxR-autoinducer is situated near a promoter such that its binding prevents the binding of RNA polymerase, then it becomes a repressor. Over two thousand-fold induction has been achieved with this strategy using lac repressor and its operator (Lanzer and Bujard 1988).

The lac system is controlled by inducers, usually isopropylthio-β-galactoside (IPTG) or allolactose, which, when bound to the lac repressor, reduce its affinity for the lac operator, thereby relieving repression. However, if LuxR were used as a repressor, its effector (autoinducer) would act as a co-repressor, much like L-tryptophan does with the trp repressor. The trp repressor-operator system can be "induced" if 3-β-indoleacrylic acid (IAA), a tryptophan analogue, is administered while sufficient L-tryptophan is present in the cell to cause repression (Joachimiak et al. 1983). The IAA competes with L-tryptophan for the trp repressor but the repressor-IAA complex does not bind tightly to the trp operator, so repression is relieved.

Eberhard and co-workers have synthesized autoinducer analogues and have shown several of these to be potent competitive inhibitors of autoinducer in *Vibrio fischeri* (Eberhard et al. 1986). It is possible that one or more of the analogues, like IAA with the trp repressor, could relieve repression by LuxR. If this approach proves impractical, relief of repression can be accomplished by harvesting the cells and resuspending them in fresh, autoinducer-free, culture medium.

The advantage of the LuxR "repressor" configuration is that one can make use of the specificity of LuxR for its economical, non-metabolizable effectors without relying on the specific protein-protein contacts between LuxR and prokaryotic RNA polymerases that are needed for transcriptional activation. Because only DNA binding is required of LuxR for repression, and because of the apparent permeability of membranes to autoinducer, this technology and its benefits could be extended to distantly related prokaryotic systems (e.g. gram-positive bacteria) and perhaps even to eukaryotic systems like yeast and cultured animal or plant cells.

In a highly preferred embodiment of the present invention, the lux regulatory circuit consists of a luxR gene derived from the operon$_L$ of a lux regulatory circuit. The luxR gene is under regulation of the control region of the lux regulatory circuit and operably linked to it. The lux control region is further connected to a portion of operon$_R$. The rightward operon normally consists of intact and sequentially oriented genes, luxIC-DABE, but in this highly preferred embodiment the operon only retains a truncated luxI gene in order to disrupt the normal positive feedback associated with the rightward operon. The lux regulatory region of the present invention may be obtained from a number of different bioluminescent bacteria as will be well understood by those of skill in the art. In certain preferred embodiments, the lux regulatory circuit is isolated from *Vibrio fischeri*.

The expression system of the present invention is designed to allow expression of any deleterious gene products. However, in certain preferred embodiments the expression system may be used to express the product of a gene which, when expressed, is lethal to the host cell. Expression of a particularly lethal gene is provided in a preferred embodiment where lysis genes S, R and R$_z$ of bacteriophage λ are expressed using the expression system of the present invention. Similar genes would include the lysis genes of the MS2 virus and the lytic peptides of the enteric bacteria such as colicins.

Additionally, the expression system of the present invention is designed such that induction of expression is controlled by addition of an inducer to the environment of the host cells containing the expression system. Naturally occurring inducer may be used. In one embodiment, naturally occurring autoinducer produced endogenously within the host cell carrying the expression system of the present invention may be achieved as a function of the density of the host cells in culture. Since luxI, whose product is necessary for the synthesis of endogenously-produced autoinducer, is the first gene in operon$_R$, LuxR stimulation leads to the synthesis of more autoinducer and a positive feedback loop is created leading to a sharp induction of operon$_R$. The timing of induction is therefore a function of the basal level of rightward transcription, which determines the rate of initial accumulation of autoinducer. Vectors containing the intact luxR and luxI genes will allow the density-dependent regulation to be imposed on a target gene cloned downstream of luxI in operon$_R$. The timing of induction can then be altered through mutagenesis of the rightward promoter, allowing variable basal levels of transcription to be achieved and induction of the target gene to occur at a chosen cell density.

However, in a preferred embodiment, the inducer will be an exogenously added inducer. In general and overall embodiments, the inducer must be able to induce the expression of the leftward operon to a degree adequate to initiate transcription in the rightward operon (See, e.g., Eberhard et al. 1986 for functional analogs). In a most preferred embodiment, the inducer will be the inexpensive and readily-synthesized molecule, N-(3-oxo-hexanoyl) homoserine lactone. In other embodiments, the inducer will be an autoinducer characterized as a small diffusible molecule capable of the requisite capability to control expression in combination with the regulatory circuits of the present invention.

It is, of course, possible to use the expression system of the present invention in the native Vibrio host or in related bacterial species. However, in a preferred embodiment, the expression system will be used in conjunction with *Escherichia coli* cells.

The present invention also relates to construction of vectors designed to carry lux regulatory circuitry associated with the expression systems of the invention. In a preferred construction, such vectors will contain a truncated luxI gene functionally connected to a multiple cloning site downstream of the truncated portion. Such multiple cloning sites are well known in the art and consist of a number of restriction endonuclease sites for ease of cloning gene-containing fragments downstream of the luxI truncation.

A method for expression of a deleterious gene is provided by the present invention as well. The steps include constructing a vector with a lux regulatory circuit, functionally connecting a deleterious gene to the lux regulatory circuit, transforming the vector containing the regulatory circuit and deleterious gene into a host cell and growing the resulting host cells to a late phase of growth in which there are many such cells with many such vectors and then inducing expression of the deleterious gene by adding an exogenous inducer to the growth medium of the bacterial culture.

BRIEF DESCRIPTION OF THE DRAWINGS

FIG. 1. Construction of the lysis vector pGS102. Small arrows indicate the 5'-to-3' direction of the gene indicated, and large arrows indicate cloning steps taken during the construction of the pGS102 plasmid (kb=Kilobases). Deletion of the DNA segment from SnaBI to BalI shown in pGS102 results in the preferred construction pGS103.

DESCRIPTION OF PREFERRED EMBODIMENTS

The following examples describe, in detail, the steps required to practice the present invention and demonstrate the utility of the expression system of the present invention when used in combination with a very lethal gene product, the lysis genes of λ bacteriophage. In particular, the construction of a plasmid vector which retains an intact luxR gene and regulatory region but lacks all of the genes in the operon$_R$, retaining only a truncated luxI gene is described. This arrangement resulted in an expression system in which operon$_R$ transcription is controlled by the addition of synthetic autoinducer but which lacks the positive-feedback mechanism. The potentially lethal transcriptional fusion of the lysis genes (S,R,R$_z$) from bacteriophage λ was created in operon$_R$ by insertion downstream of the truncated luxI gene demonstrating the utility of the invention for the expression of a very lethal lytic gene product. In another demonstration of the utility of the present invention, vector (pGS102) was used in a lethal genetic selection in conjunction with a subsequent luminescence screen to recover point mutations in the luxR gene.

EXAMPLE I

Enzymes and chemicals. Restriction enzymes and T4 DNA ligase were purchased from New England Biolabs, Inc., or Boehringer Mannheim Biochemicals. Klenow fragment of *E. coli* DNA polymerase I and modified T7 DNA polymerase (Sequenase) were purchased from United States Biochemicals. ATP and deoxyribonucleotides were obtained from Pharmacia LKB. Radiolabeled dATP was obtained from Dupont, NEN Research Products. Hydroxylamine hydrochloride and n-decanal were obtained from Sigma Chemical Co. All other chemicals were of the highest quality commercially available.

Cell strains. All growth experiments were performed using *E. coli* TB1 [hsdR Δ(lac pro)]. *E. coli* CA8404 (crp* was a gift of Pete Greenberg, but is readily obtainable by methods known well to those of skill in the art) was used to achieve better complementation with luxR in trans. This strain produces a mutant CAP which does not require cAMP to activate transcription from cAMP-CAP-regulated promoters.

Plasmid constructions. Construction of the lysis vector pGS102 is summarized in FIG. 1. pGS102 was constructed from the plasmid pSB101, which contains a BglII restriction fragment harboring the bioluminescence genes luxR, -I, -C, and -D' cloned into the BamHI site of pBR322 with the transcription of operon$_R$ oriented opposite that of the tet gene. To eliminate production of the autoinducer via the luxI gene product, pSB101 was digested with ClaI, filled with Klenow fragment, partially digested with HincII, and ligated to yield plasmid pSB103 containing a truncated luxI gene fused at the ClaI site of pSB101. The lysis genes of bacteriophage λ (S, R, and R$_z$) were isolated on a 1.5-kilobase EcoRI restriction fragment from plasmid pSRI, which is a derivative of plasmid pRGI (Raab et al. 1986) with the unique HindIII site converted to an EcoRI site by using synthetic adapters. This EcoRI fragment was subsequently ligated into the EcoRI site of pSB103 to yield pGS102. Restriction analysis was used to screen for the proper orientation of the lysis genes in the pGS102 construction which generated a transcriptional fusion between operon$_R$ of the *V. fischeri* lux genes and the λ lysis genes, which were now located downstream of the truncated luxI gene.

A SnaBI-BalI deletion of pGS102 was constructed to remove *V. fischeri* DNA that was downstream of the luxR gene in the operon$_L$. This construction was called pGS103 and exhibited the same lysis phenotype as pGS102.

The construction of plasmid pJHD500 has been described earlier (Devine et al. 1989). This plasmid is similar to pGS102, except the lux A and luxB genes, encoding the subunits for the luciferase enzyme from *Vibrio harveyi*, were cloned downstream of the truncated luxI gene, creating a bioluminescent transcriptional reporter for operon$_R$. DNA containing mutations in the luxR gene generated in pGS102 and pGS103 were subcloned into pJHD500 in order to quantitate the ability of the mutant LuxR proteins to stimulate rightward transcription.

Growth of cultures and measurement of the Extent of Cell Lysis. The ability of the mutant LuxR proteins to respond to autoinducer was determined by monitoring cell growth and aldehyde-stimulatable luminescence of samples withdrawn from cultures grown in 50-ml culture flasks containing (initially) 12 ml of Luria-Bertani (LB) medium with carbenicillin (100 μg/ml) at 30° C. in a New Brunswick model G76 gyratory water bath shaker at 200 rpm. Inoculation was from overnight cultures grown at 30° C. and diluted 1/200 (vol/vol). Samples (1 ml) were removed at various times during growth. Cell density was determined as the optical density at 600 nm (OD$_{600}$) by using a Milton Roy Spectronic 601 spectrophotometer. The same samples were then used for luminescence measurements in vivo by transferring the sample into a 20-ml scintillation vial, placing the vial in a photometer, and injecting 1 ml of a sonicated solution of n-decanal (10 μl of aldehyde per 10 ml of LB medium). Peak light emission was monitored by using a photomultiplier-photometer for which 1 light unit represents $9.8 \times 10^9$ quanta/s, based on the liquid light standard of Hastings and Weber (1963).

Data depicting cell lysis were collected by monitoring culture growth in 125-ml culture flasks containing 20 ml of LB medium with carbenicillin (100 μg/ml) at 30° C. in a New Brunswick Aquatherm water bath with shaking at 100 rpm. Duplicate cultures were inoculated by dilution (1/200 [vol/vol]) of an overnight culture grown at 30° C. with an additional of autoinducer of one of the cultures immediately after inoculation. Cell lysis was detected as a drop in the OD$_{600}$ of the culture.

Pure autoinducer was synthesized by the method of Eberhard et al. (Eberhard et al. 1981) and was stored as a 50 mM solution in water at 4° C. This stock was further diluted into the growth medium to the desired concentration. The concentration of autoinducer was calculated by using the weight of the dried, purified material and a molecular mass of 213 g/mol for autoinducer.

Colonies containing pJHD500 and its luxR mutant derivatives were screened for luminescence on solid medium by applying n-decanal to the lid of a petri dish and observing the glowing colonies in a dark room.

It is important to note that certain problems were encountered in this study while adapting the lysis method to the lux system which were mainly a result of different temperature requirements for the lux system isolated from a marine bacterium, and the lysis genes which normally function in the enteric bacterium *E. coli*. For example, when *E. coli* carrying a lysis plasmid was grown at 37° C., cell lysis was observed in the absence of autoinducer. However, cell lysis was not observed in the absence of autoinducer when the cultures were grown at 30° C. or lower. This apparently resulted from either an increased basal level of transcription of operon$_R$ at 37° C. or the ability of the protein products of lysis genes to function more efficiently at the higher temperatures. Temperature therefore appears to be one parameter which can be adjusted to optimize the conditions for the lysis selection and may provide a means for controlling the lethality of the lysis genes, allowing selection of a variety of mutants.

Mutant selection in liquid medium. A variety of growth conditions were used for lysis selection in liquid medium. Temperatures were varied between 24° and 37° C., and M9 minimal medium supplemented with glycerol (0.2%), proline (40 μg/ml), and thiamine (0.001%) was used as well as LB medium. Autoinducer concentrations were varied between 0.5 and 5 μM. In all experiments, 5-ml cultures of *E. coli* TB1 containing plasmid pGS102, prepared by inoculation from overnight cultures by dilution (1/100) into medium containing carbenicillin (100 μg/ml), were used. Duplicate cultures were incubated with and without autoinducer until cell lysis was observed visually as a loss of the turbidity of the culture. Cultures were then diluted into fresh medium, plated onto solid LB medium, and incubated at 30° C. to allow growth of surviving cells. In some cases, the lysed cultures were pelleted, resuspended in fresh autoinducer-containing medium, and taken through a second lysis induction (double-induction experiment).

Hydroxylamine mutagenesis and screening on solid medium. Hydroxylamine mutagenesis was done essentially as described previously (Humphreys et al. 1976). Purified pGS103 (2.5 μg) was suspended in 250 μl of a 1M hydroxylamine solution at pH 6.0. The hydroxylamine solution was prepared by mixing 125 μl each of a 2M hydroxylamine solution (0.7 g of hydroxylamine hydrochloride dissolved in 0.56 ml of 4N NaOH and adjusted to 5 ml with sterile water) and a 2×TE solution (200 mM Tris Cl, pH 6.0, 2 mM EDTA). This mutagenesis mixture was incubated at 65° C. for 35 min, and the modified DNA was precipitated with 2 volumes of ethanol after the addition of ammonium acetate to 1M. The pellet was suspended in TE (pH 8.0), and 0.25 μg was used to transform competent *E. coli* TB1. Transformed cells were plated in duplicate onto solid LB medium containing carbenicillin (100 μg/ml) with and without 5 μM autoinducer. Mutant colonies were screened as normal opaque colonies on autoinducer-containing plates against a background of translucent colonies (see, Example II, infra).

DNA sequencing. Double-stranded plasmid DNA was prepared from overnight cultures by the alkaline lysis method (Maniatis et al. 1982). The DNA pellets were then treated with RNase A and precipitated with polyethylene glycol 8000. The purified DNA was then denatured with NaOH and used as template for sequencing by the dideoxy-chain termination method using modified T7 DNA polymerase (Sequenase) (Tabor and Richardson 1987). Sequencing primers used to sequence luxR have been described elsewhere (Devine et al. 1989).

Site-directed mutagenesis. Site-directed mutagenesis was done by the method of Kunkel et al. (1987), with slight variations. Single-stranded uracil-containing DNA isolated from phagemid-infected cells was used as a template for the mutagenesis reactions. Purification of the template was done as described earlier (Devine et al. 1989), except the starting plasmid was pVFS185, which is a derivative of pTZ18R (Pharmacia) containing a SacI restriction fragment harboring most of luxR, all of luxI and luxC, and a portion of luxD.

EXAMPLE II

Figure 1:
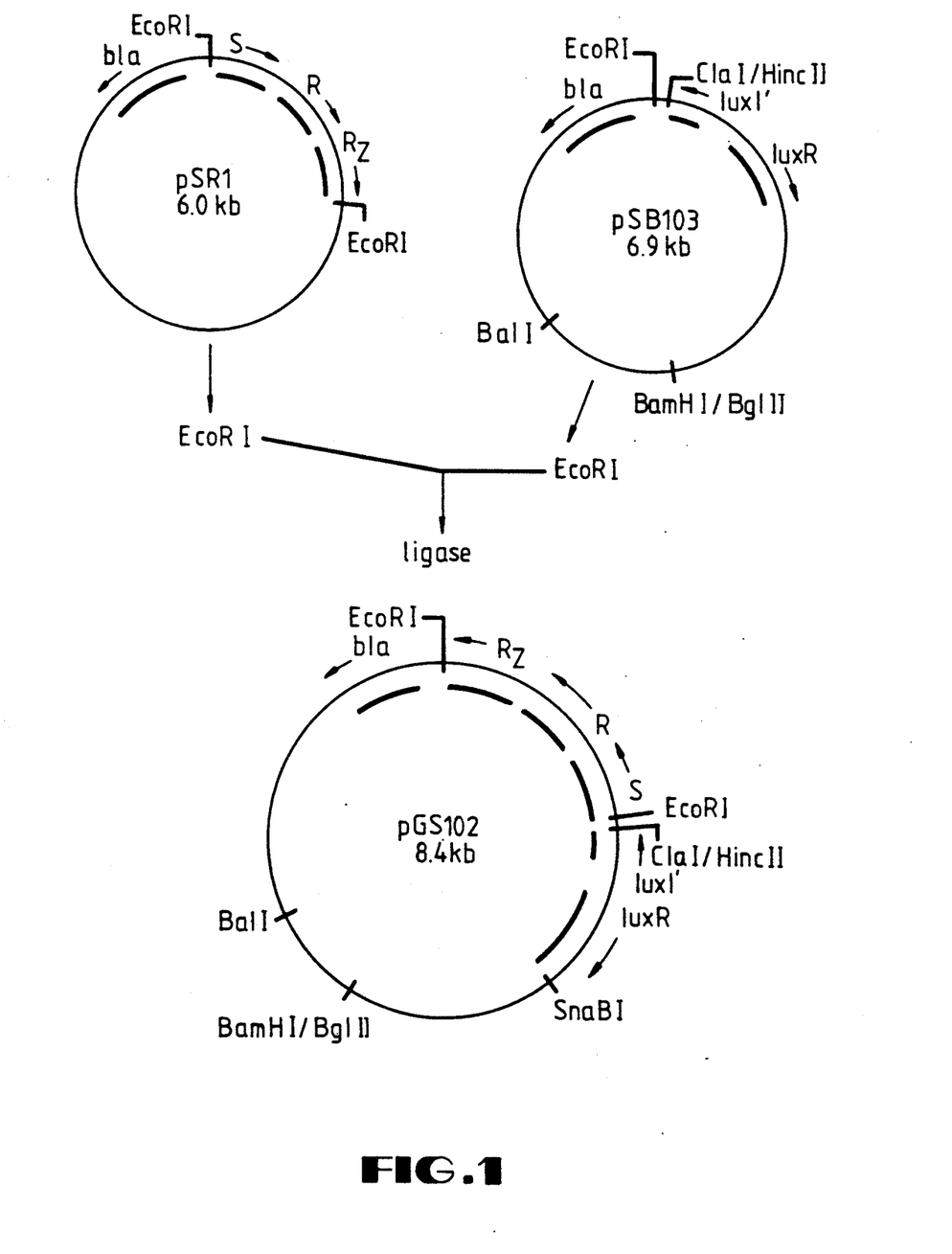

Demonstration that the lysis phenotype is under lux control. The lysis vectors pGS102 and pGS103 both allowed expression of the lysis phenotype to be controlled by the addition of synthetic autoinducer. A SnaBI-BalI deletion of pGS102 was done to create pGS103 (FIG. 1). The deleted sequences consisted of uncharacterized *V. fischeri* DNA and a portion of the pBR322 vector. Removal of these sequences had no effect on the induction of cell lysis by the addition of autoinducer. A Budapest Treaty Deposit was made prior to the filing of the present patent application with the United States Patent and Trademark Office to the American Type Culture Collection of pGS103 and that deposit has been assigned accession number ATCC 40830.

Figure 2:
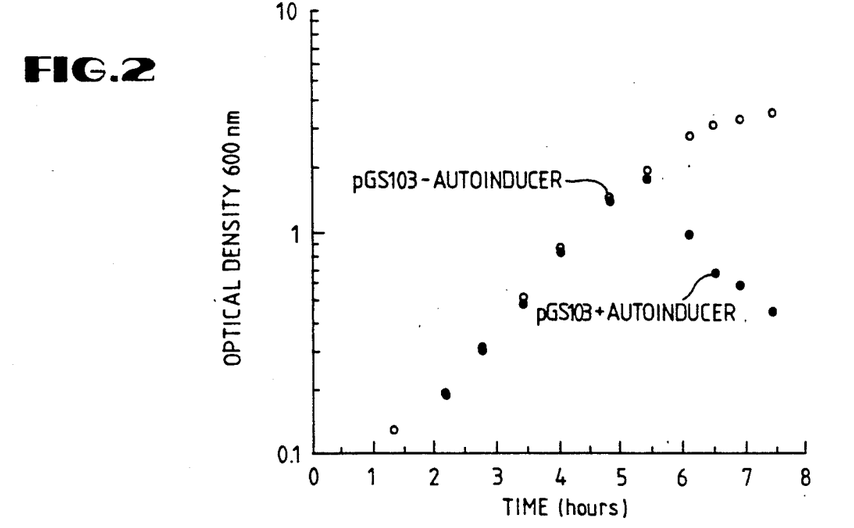
FIG. 2. Growth of cultures of *E. coli* TB1 carrying the plasmid pGS103 and demonstration of autoinducer-dependent cell lysis. Autoinducer (5 μM) was added from the beginning of the experiment where indicated.

When autoinducer was added from the beginning of the growth experience or at an early point in growth, a lag was observed prior to cell lysis while LuxR protein accumulated. A typical lysis curve is shown in FIG. 2. At 30° C. in LB medium, with autoinducer added at the beginning of the experiment, cell lysis was observed as a decrease in the $OD_{600}$ of the culture between 4.5 and 5 h after initial inoculation of the culture ($OD_{600}$, 1.2), followed by a steady decrease in $OD_{600}$ during the next several hours. When autoinducer was added at a later point during culture growth, the lag period was decreased. The lag could be almost completely eliminated if *E. coli* CRP* was used, since the stimulation of luxR expression by cAMP-CAP does not require the accumulation of cAMP in this strain (data not shown). These observations suggest that the timing of induction was mainly a function of the cAMp-CAp stimulation of luxR expression.

Selection of mutants following lysis induction in liquid medium. Selection of lux regulatory mutants was accomplished by the addition of autoinducer to cultures grown in liquid medium at 24° C. and allowing the culture to incubate overnight (12 to 14 h) with shaking. Cells surviving the lysis induction were then grown on solid medium. Two problems were encountered with this procedure. First, a background of colonies was observed which retained the ability to lyse when screened in liquid medium for a nonlysing phenotype. Second, a considerable proportion of the colonies isolated from the selection which did retain a nonlysing phenotype carried plasmids which had suffered deletions and/or other rearrangements of the original pGS102 plasmid. The former problem was partially eliminated by pelleting the cells from the initial lysis induction, suspending them in fresh autoinducer-containing medium, and taking them through a second lysis induction under identical conditions. Dilutions plated from these cultures exhibited a lower background of surviving nonmutant colonies.

From the double-induction experiment in M9 medium at 24° C., 18 colonies, which were presumably mutant, were picked and grown overnight to isolate of plasmid DNA and to screen for a nonlysing phenotype in liquid medium. All 18 mutants exhibited a nonlysing phenotype, and 13 of these 18 isolates had wild-type restrictions patterns for the pGS102 plasmid. To screen for mutations which were not plasmid-borne, the plasmid DNA from the remaining 13 mutants was retransformed into wild-type *E. coli* and again screened for lysis in response to autoinducer in liquid medium. By this criterion, six of these mutants (L2S2, L2S9, L2S14, L2S18, L2S20, and L2S21) were results of non-plasmid borne mutations and were probably results of *E. coli* chromosomal mutations which prevented cell lysis. The remaining seven mutants were judged to be plasmid borne and were next screened for luxR null phenotypes by checking for lysis in the presence of autoinducer with luxR supplied in trans on a compatible plasmid (pAC102). All seven of the mutants (L2S3, L2S5, L2S7, L2S8, L2S10, L2S15, and L2S17) exhibited a luxR null phenotype. The nucleotide sequences of the luxR genes from the luxR null mutants were determined, and the results are shown in Table 1. No mutation was identified within the luxR coding region for the L2S10 and L2S15 isolates.

TABLE 1

Summary of luxR point mutations isolated by variations of the lysis selection

| Mutation designation | luxR nucleotide change[a] | LuxR amino acid change | Lysis selection[b] |
|---|---|---|---|
| L2S3 | T-114 to A | C-38 to TGA (stop) | L |
| L2S5 | G-325 to T | V109L | L |
| L2S7 | G-368 to T | S123I | L |
| L2S8 | G-352 to T | L118F | L |
| L2S17 | T-502 to G | Y-169 to TAG (stop) | L |
|  | C-508 to A | R170R (silent) |  |
| XS-2 | G-244 to A | V82I | S |
| XS-3 | C-649 to T | H217Y | S |
| XS-4 | G-235 to A | D79N | S |

[a]Positions are numbered from 1 starting with the A of the AUG start codon for luxR indicated by Devine et al. (1988).
[b]L, Lysis selection in liquid medium; S, lysis screen on solid medium after hydroxylamine mutagenesis (see, Example I, supra).

Hydroxylamine mutagenesis and lysis screen on solid medium. Attempts to select mutants by the lysis technique on autoinducer containing solid medium resulted, as with the liquid medium selection, in a large background of colonies which retained a lysing phenotype when screened in liquid medium. The desired mutant colonies could, however, be discriminated from the background of surviving nonmutant colonies as a normal versus translucent phenotype. The translucent phenotype was presumably due to a heterogeneous population of lysed and unlysed cells. In order to increase the frequency of mutant colonies, the plasmid pGS103 was modified by reaction with hydroxylamine in vitro prior to screening for mutants on autoinducer-containing solid medium. By this method, approximately 15% of the colonies were of the mutant phenotype in the hydroxylamine experiment, whereas in the control experiment of unmodified plasmid, mutant colonies were observed only at very low frequencies. Twenty mutant colonies were isolated with this screen, and plasmid DNA was prepared for further study.

Quantitation of autoinducer response of luxR point mutations. To recover mutations of the luxR gene, restriction fragments containing portions of the luxR gene from the 20 mutants isolated by the hydroxylamine experiment described above were subcloned into the bioluminescent rightward reporter vector pJHD500 and screened as dim colonies on autoinducer-containing solid medium. Colonies of cells containing pJHD500 with a wild-type luxR were bright under these conditions. Eight dim mutants were picked from this screen, five of which possessed a wild-type restriction pattern, indicating an intact luxR gene. Three of these were sequenced and shown to contain point mutations in luxR resulting in changes in the LuxR amino acid sequence of Val at position 82 to Ile, hereinafter designated as V82I, H217Y, and D79N (Table 1). In addition, the three missense mutations and the L2S3 nonsense mutation isolated by the liquid lysis induction were subcloned into pJHD500 to allow transcription from operon$_R$ to be measured. To screen for mutations which could respond to higher concentrations of autoinducer, cells containing the luxR mutant derivatives of pJHD500 were replica plated onto solid medium with and without 5 μM autoinducer. The LuxR protein with the amino acid change of V82I was the only mutant observed by a visual screen to respond to this (elevated) concentration of autoinducer. To further examine the autoinducer response of the change at position 82, a second mutation was introduced by site-directed mutagenesis which changed the valine at this position to leucine instead of isoleucine.

A similar genetic study of the LuxR protein from *V. fischeri* MJ1 has been reported by Slock et al. (1990). These authors describe the isolation of several LuxR missense mutations, one of which was observed to respond to higher concentrations of autoinducer. This mutation resulted in the replacement of the histidine at position 127 with tyrosine. In order to quantitate the autoinducer response of this mutation without reporter vector, the same mutation was constructed by site-directed mutagenesis and subcloned into pJHD500. The change was introduced by site-directed mutagenesis rather than by subcloning of the Slock et al. (1990) mutation because of the two different strains of *V. fischeri* which were used (ATCC 7744 and MJ1) and which have been shown to have differences in the amino acid sequence at four positions within the LuxR protein (Devine et al. 1989). Thus, the present inventors wanted to ensure that the observed phenotype was the result of the change at position 127 and not due to strain differences in the LuxR protein.

Figure 3:
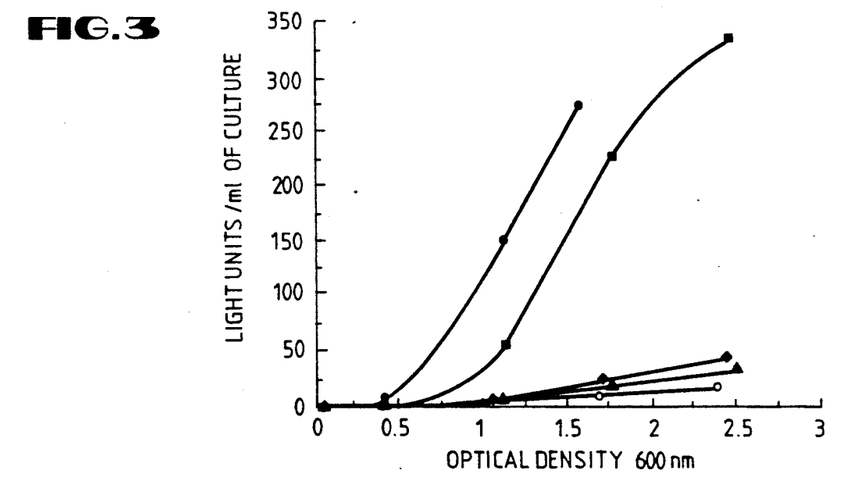
FIG. 3. Autoinducer response of pJHD500 and three LuxR⁻ pJHD500 derivatives, Symbols: ● and ○, pJHD500-wild type LuxR; ■, H127Y; ◆ V82L; ▲, V82I. Open symbols indicate no autoinducer added to the culture, and closed symbols indicate the addition of 2.5 μM autoinducer from the beginning of the experiment.

Growth curves and luciferase assays in vivo were done for the total of nine luxR mutations cloned in the reporter vector pJHD500. The autoinducer response was measured as the ability of the mutations to stimulate operon$_R$ transcription in the presence of autoinducer (2.5 μM) above the basal level observed in the absence of autoinducer. The results are summarized in Table 2, and complete growth curves of those mutations which respond to autoinducer are shown in FIG. 3. The results presented in FIG. 3 and Table 2 demonstrate that the change of V82I responded with an activity of approximately 70% that of the wild-type protein (23-versus 33-fold stimulation above the basal level at an OD$_{600}$ of 1.5). The site-directed changes of V82L and H127Y responded to a much lower extent, giving only 8 and 6% of the stimulation of the wild-type protein, respectively. The change of D79N was observed to reproducibly give stimulation of about 1% that of the wild-type protein at a 10-fold-higher autoinducer concentration than that used in the above experiments (data not shown). Both of the position 82 mutants, as well as the H127Y mutant, were screened for response to a range of autoinducer concentrations. With all three of these variants, it was found that elevated levels of autoinducer were required to compensate for the lesion (data not shown). None of the remaining mutations exhibited significant autoinducer-dependent stimulation (Table 2).

TABLE 2

Autoinducer response of luxR point mutations measured in the transcriptional reporter vector pJHD500

| LuxR variant of pJHD500 | Light units/ml[a] | | Stimulation (fold) | % Stimulation[b] |
|---|---|---|---|---|
| | Without autoinducer | With autoinducer (2.5 μM) | | |
| pJHD500 | 8.0 | 265 | 33 | 100 |
| L2S3 | 9.0 | 9.0 | None | 0 |
| D79N | 9.0 | 10.0 | None | 0[c] |
| V82I | 7.5 | 175 | 23 | 70 |
| V82L | 8.0 | 20.0 | 2.5 | 8 |
| V109L | 7.0 | 8.0 | None | 0 |
| L118F | 8.0 | 8.0 | None | 0 |
| S123I | 6.5 | 6.0 | None | 0 |
| H127Y | 8.0 | 15.0 | 1.9 | 6 |
| H217Y[d] | 2.0 | 2.3 | None | 0 |

[a] Peak light emission measured from 1 ml of culture at an $OC_{600}$ of 1.5.
[b] Values are given relative to the stimulation achieved by the wild-type LuxR protein encoded by the pJHD500 construction.
[c] At a 10-fold-higher autoinducer concentration, the response of D79N is about 1% that of the wild-type protein.
[d] The H217Y data were collected during a different growth experiment under a different set of conditions than was used for the other mutations shown in Table 1 (100 rpm, 29° C., 2.5 μM autoinducer).

Figure 4:
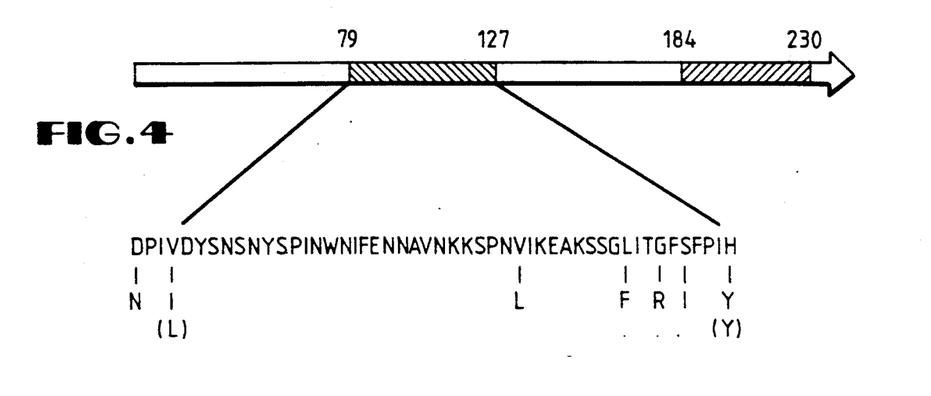
FIG. 4. Critical regions of the LuxR protein defined by random mutagenesis and the primary sequence of the autoinducer-binding region (■). Boldface type indicates random mutations isolated in this study which map between residues 79 and 127. Open type indicates random mutations isolated by Slock et al. (1990) which map between residues 79 and 127. Letters in parentheses indicate amino acid changes introduced by site-directed mutagenesis. The second critical region is defined by mutations isolated by Slock, et al. (1990) and the H217Y mutation isolated in this study (✲).

Location of random mutations in luxR. The locations of the randomly generated mutations isolated in this study are shown in FIG. 4 along with two mutations isolated by Slock et al. (1990), G121R and H127Y, which reside in the same region of the LuxR primary sequence. A total of seven randomly generated missense mutations occur within a 49-amino-acid stretch of the LuxR protein spanning residues 79 to 127 labeled as the autoinducer-binding region in FIG. 4 (see, Example III, infra). One mutation isolated during the luminescence screen, H217Y, occurred within a second critical region in LuxR spanning residues 184 to 230 and defined primarily by mutations isolated by Slock et al. (1990) (FIG. 4).

EXAMPLE III

Several features of the lysis gene cassette from bacteriophage λ make it generally useful as the lethal component in a lethal genetic selection. The results of an exhaustive mutational analysis of the bacteriophage λ S gene revealed that host mutations which confer resistance to the lethal action of the S protein are not recovered, since the S protein apparently acts alone in forming the lethal pore in the cytoplasmic membrane (Raab et al. 1986). This is not true for many other lethal proteins, which require interaction with host components in order to exert their lethal functions. The S gene is the only lethal gene of the three comprising the lysis cassette, and it consists of only 107 codons. The small size of the S gene makes it a small target for mutation, and therefore, the frequency of recovering mutations in the lysis cassette which prevent lethality is very low. In addition, many of the codons constituting the S gene are not mutable by transitions to "knockout" missense mutations or non-sense mutations which result in loss of S protein function. Lastly, a simple secondary screen can distinguish between the desired transcriptional control mutants and unwanted S gene mutants. This screen utilizes the ability of a limited amount of chloroform to substitute for S protein pore formation by disrupting the cell membrane and allowing the diffusion of accumulated murein transglycosylase into the periplasm (Goldberg and Howe 1969). The murein transglycosylase, the product of the λ R gene, is responsible for degradation of the peptidoglycan in the E. coli cell wall (Bienkowska-Szewczyk et al. 1981). Transglycosylase accumulation does not require S gene function; therefore, mutations which decrease transcription of the lysis cassette will not lyse even in the presence of chloroform, while mutations in the S gene will allow lysis in the presence of chloroform since the transglycosylase can still accumulate and is free to enter the periplasm.

In this study, the λ lysis cassette was used to isolate mutations in the luxR gene from V. fischeri with E. coli as a host for the cloned lux genes. A transcriptional fusion was created between the bacteriophage λ lysis genes and operon$_R$ by insertion downstream of a truncated luxI gene. The resulting plasmid allowed cell lysis to be controlled by the addition of synthetic autoinducer to the growth medium. Mutations in the luxR gene generated by variations of this lysis selection were subcloned into the luminescent reporter vector pJHD500, which created both a secondary screen for defective LuxR proteins and a method for quantitating the ability of these LuxR variants to respond to autoinducer.

A total of seven randomly generated missense mutations have been characterized, and by DNA sequence analysis, the lesions have been shown to occur within a 49-amino-acid stretch of the LuxR primary sequence. An additional mutation introduced by site-directed mutagenesis changed the valine at position 82 to leucine. A change of valine to isoleucine at position 82 of LuxR resulted in a protein with 70% of the autoinducer-dependent transcriptional stimulation capacity of the wild-type protein, while changing this same valine to a leucine resulted in a protein exhibiting only 8% of the wild-type response (Table 2). The ability of such conservative changes at position 82 of LuxR, valine to isoleucine and valine to leucine, to dramatically affect the autoinducer response of the resulting proteins suggests that this residue may be involved in direct interaction with the autoinducer molecule. A total of four luxR mutations yielded proteins which exhibited an ability to stimulate transcription of operon$_R$, albeit to lower-than-wild-type levels, while the remaining luxR mutations did not allow any detectable autoinducer-dependent stimulation, even at elevated concentrations of autoinducer. The clustering of the seven randomly generated mutations within the region spanning residues 79 to 127 of the LuxR protein demonstrates that this region of the protein is critical for activity. The ability of several mutations within this region to respond to elevated concentrations of autoinducer suggests that the autoinducer-binding site is composed, at least in part, of amino acids residing within this region.

The possibility that the mutations in the proposed autoinducer-binding region may result in the production of unstable proteins which could give rise to the defective autoinducer response phenotype observed cannot be ruled out by the data of the present invention. However, two additional mutations isolated by Slock et al. (1990), G121R and H127Y, were shown by Western immunoblot analysis to be synthesized in vivo at levels comparable to those of the wild-type protein. These results increase the likelihood that the mutant proteins of the present invention are likewise produced at wild-type levels. This is especially true of the mutations at position 82 of luxR which both give stimulation greater than does the H127Y protein, which is synthesized at wild-type levels. It is difficult to imagine a situation in which the proteins with position 82 mutations could give greater stimulation if they were synthesized at levels lower than wild-type levels.

The results of this mutational study of the LuxR protein, coupled with those of Slock et al. (1990), demonstrate that at least two functional regions exist in the LuxR protein. One region spans amino acids 79 to 127 and is proposed to be an autoinducer-binding region, and the other region spans amino acids 184 to 230 (FIG. 4). Although no experimental evidence demonstrates that the mutations isolated by Slock et al. (1990) and the mutation of H217Y isolated in this study, which resides in this second critical region, are in fact defective in DNA binding, there is some recent evidence which supports the hypothesis that a carboxy-terminal DNA-binding region exists in LuxR. Alignment of amino acid sequences similar to those of the LuxR protein by Henikoff et al. (1990) revealed that a carboxy-terminal region of LuxR has a sequence similar to regions within nine other diverse bacterial proteins, including five known activator proteins (FixJ from *Rhizobium meliloti*, MalT and UhpA from *E. coli*, GerE from *Bacillus subtilis*, and RcsA from *Klebsiella aerogenes*). The apparently homologous regions revealed have been predicted to form a helix-turn-helix DNA-binding motif at a common position which includes residues within the region defined by mutations residing between positions 184 and 230 in LuxR. Further biochemical evidence is required, however, before this region can be unequivocally defined as the DNA-binding region of the LuxR protein.

The primary regulatory circuit controlling the induction of bioluminescence in *V. fischeri* appears to require three interacting elements: the LuxR protein, the autoinducer molecule, and the lux operator. Early genetic studies in which lux regulatory functions were deleted by transposon insertion mutagenesis demonstrated that the luxR and luxI genes were both required for the proper induction of bioluminescence (Engebrecht et al. 1983). Insertions in luxR resulted in loss of a function which could not be recovered by the addition of autoinducer, whereas insertions in the luxI gene were complemented by autoinducer addition. These observations led to a model which suggested that the luxI gene product was required for autoinducer synthesis and that the luxR gene product interacted with the autoinducer molecule to stimulate transcription of operon$_R$. Recent studies supported that model and demonstrated that a 20-base-pair palindrome, the lux operator, located within the control region is also required for autoinducer-dependent stimulation of transcription of operon$_R$ (Devine et al 1989). Several mutations in the luxR gene which encoded variant LuxR proteins with altered autoinducer responses have been isolated in this manner. Demonstration that these mutant proteins can respond to higher concentrations of autoinducer provide the first evidence supporting the direct interaction between LuxR and autoinducer (Shadel et al. 1990).

REFERENCES CITED

The following references to the extent that they provide procedural details supplementary to those set forth herein, are specifically incorporated herein by reference.

1. Adhya, et al. 1971. pp. 743-746, The Role of Gene S. In, P. R. Hershey, (ed.), The Bacteriophage Lambda. Cold Spring Harbor Laboratory, Cold Spring Harbor, N.Y.
2. Baldwin et al. 1989. *J. Biolumin. Chemilumin.* 4:326-341.
3. Bedwell and Nomura. 1986. *Mol. Gen. Genet.* 204:17-23.
4. Bienkowska-Szewczyk, et al. 1981. *Mol. Gen. Genet.* 184:1112-1114.
5. Coleman, et al. 1983. *J. Bacteriol.* 153:1098-1110.
6. Devine, et al. 1988. *Biochemistry* 27:837-842.
7. Devine, et al. 1989. *Proc. Natl. Acad. Sci USA* 86:5688-5692.
8. Dunlap and Greenberg. 1985. *J. Bacteriol.* 164:45-50.
9. Dunlap and Greenberg. 1988. *J. Bacteriol.* 170:4040-4046.
10. Eberhard. 1972. *Bacteriol.* 109:1101-1105.
11. Eberhard, et al. 1981. *Biochemistry* 20:2444-2449.
12. Eberhard, et al. 1986. *Arch. Microbiol.* 146:35-40.
13. Engebrecht, et al. 1983. Cell 32: 773-781.
14. Engebrecht and Silverman. 1984. *Proc. Natl. Acad. Sci. USA* 81:4154-4158.
15. Engebrecht and Silverman. 1986. Regulation of expression of bacterial genes for bioluminescence, p. 31-44, In J. K. Setlow and A. Hollaender (eds.), *Genetic Engineering*, vol. 8. Plenum Publishing Corp., New York.
16. Engebrecht and Silverman. 1987. *Nucleic Acids Res.* 15:10455-10467.
17. Goldberg and Howe. 1969. *Virology* 38:200-202.
18. Hastings and Weber. 1963. *J. Opt. Soc. Am.* 53:1410-1415.
19. Henikoff et al 1990. *Methods Enzymol* 183:111-132.
20. Humphreys, et al. 1976. *Mol. Gen. Genet.* 145:101-108.
21. Joachimiak, et al. 1983. *Proc. Natl. Acad. Sci. USA* 80:668-672.
22. Kaplan, et al. 1985. *J. Labelled Compd. Radiopharm.* 22:387-395.
23. Kaplan and Greenberg. 1985. *J. Bacteriol.* 163:1210-1214.
24. Kaplan and Greenberg. 1987. *Proc. Natl. Acad. Sci. USA* 84:6639-6643.
25. Konisky. 1982. *Ann. Rev. Microbiol.* 36:125-144.
26. Kunkel, et al. 1987. *Methods Enzymol.* 154:1367-1382.
27. Lanzer and Bujard. 1988. *Proc. Natl. Acad. Sci. USA* 85:8973-8977.
28. Maniatis, et al. 1982. *Molecular cloning: a laboratory manual.* Cold Spring Harbor Laboratory, Cold Spring Harbor, N.Y.
29. Meighen. 1988. *Ann. Rev. Microbiol.* 42:151-176.
30. Michaelis and Beckwith. 1982. *Ann. Rev. Microbiol.* 36:435.
31. Raab, et al. 1986. *J. Bacteriol.* 167:1035-1041.
32. Rosenberg, et al. 1981. pp. 132-164. In, J. G. Chirikjian (ed.), Gene Amplification and Analysis.
33. Shadel, et al. 1990. *J. Bacteriol.* 172:3980-3987.
34. Slock, et al. 1990. *J. Bacteriol.* 172:3974-3979.
35. Tabor and Richardson. 1987. *Proc. Natl. Acad. Sci. USA* 84:4767-4771.
36. Ulitzur. 1989. *J. Biolumin. Chemilumin.* 4:317-325.
37. Ulitzer and Kuhn. 1988. *J. Biolumin. Chemilumin.* 2:81-93.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention.

For example, those of skill in the art will appreciate that it is possible to utilize the expression system, vectors and methods of the present invention to express genes whose products vary in their degree of toxicity to the cells in which they reside. Additionally, the regulatory circuitry that is the subject of this invention may be used directly to regulate gene expression or it may be used in an indirect manner by serving as a controlling element in combination with one or more secondary regulatory systems. In a similar manner, the expression systems, vectors and methods of the present invention may rely on induction of gene expression by addition of exogenously added inducer or may rely on endogenous autoinducer. All such modifications are intended to be included within the scope of the appended claims.

What is claimed is:

1. An expression system comprising a lux regulatory circuit, said regulatory circuit further comprising a luxR gene and truncated luxI gene of Vibrio, operably linked to and capable of stringently regulating expression of a gene, a product of which said gene is deleterious to an *Escherichia coil* host cell in which said expression system and said gene are resident.

2. The expression system of claim 1 wherein the lux regulatory circuit further comprises a luxR gene derived from the leftward operon of said lux regulatory circuit, said luxR being operably linked to a control region of said lux regulatory circuit, said control region being operably linked to a portion of a rightward operon, said rightward operon retaining a truncated luxI gene.

3. The expression system of claim 1 wherein said deleterious gene product is the product of a gene which, when expressed, is lethal to said host cell in which said expression system and said gene are resident.

4. The expression system of claim 3 wherein said gene is a lysis gene of bacteriophage λ.

5. The expression system of claim 1 wherein induction of said expression is controlled by addition of an inducer to the environment of said host cells in which said expression system is resident.

6. The expression of claim 5 wherein said inducer is an exogenously added inducer.

7. The expression of claim 5 wherein said inducer is N-(3-oxo-hexanoyl) homoserine lactone.

8. The expression of claim 1 wherein said lux regulatory circuit is operably linked to and capable of exerting control over at least one secondary regulatory system.

9. The expression system of claim 1 wherein the lux regulatory circuit further comprises a luxR gene derived from the leftward operon of said lux regulatory circuit, said luxR gene being operably linked to a control region of said lux regulatory circuit, said control region being operably linked to a portion of a rightward operon, said rightward operon comprising a promoter and a truncated luxI gene.

10. A vector comprising a lux regulatory circuit, said regulatory circuit further comprising a luxR gene and truncated luxI gene of Vibrio, operably linked to and capable of stringently regulating expression of a gene, a product of which said gene is deleterious to an *Escherichia coli* host cell in which said lux regulatory circuit and said gene are resident.

11. The vector of claim 10 wherein the lux regulatory circuit further comprises a luxR gene derived from the leftward operon of said lux regulatory circuit, said luxR being operably linked to a control region of said lux regulatory circuit, said control region being operably linked to a portion of a rightward operon, said rightward operon retaining a truncated luxI gene.

12. The vector of claim 11 wherein said truncated luxI gene is operably linked downstream of its truncated portion to a multiple cloning site.

13. The vector of claim 11 wherein the vector is pGS103.

14. A method for expression of a deleterious gene comprising:
(a) constructing a vector which is comprised of a lux regulatory circuit, said regulatory circuit further comprising a luxR gene and truncated luxI gene of Vibrio, capable of being operably linked to and capable of stringently regulating expression of said deleterious gene;
(b) operably linking said deleterious gene to said lux regulatory circuit;
(c) inserting said vector containing said lux regulatory circuit operably linked to said deleterious gene into a suitable *Escherichia coli* host cell;
(d) allowing multiplication and growth of said host cell to a suitable level; and,
(e) inducing expression of said deleterious gene by introduction of an exogenous inducer into the environment of said host cell.

15. The method of claim 14 wherein said deleterious gene produces a product which, when expressed, is lethal to said host cell.

* * * * *

UNITED STATES PATENT AND TRADEMARK OFFICE
CERTIFICATE OF CORRECTION

PATENT NO. : 5,196.318

DATED : March 23, 1993

INVENTOR(S) : Thomas O. Baldwin, et al.

It is certified that error appears in the above-identified patent and that said Letters Patent is hereby corrected as shown below:

Column 19:
    In claim 1, line 6, please delete "*coil*" and insert therefor --*coli*--.

In claim 6, line 1, please insert --system-- after "expression".

In claim 7, line 1, please insert --system-- after "expression".

Column 20:
    In claim 8, line 1, please insert --system-- after "expression".

Signed and Sealed this

Thirtieth Day of November, 1993

*Attest:*

*Attesting Officer*

BRUCE LEHMAN

*Commissioner of Patents and Trademarks*